United States Patent
Harp

(10) Patent No.: US 10,428,365 B1
(45) Date of Patent: Oct. 1, 2019

(54) QUANTITATIVE STERILE FIELD ANALYSIS SYSTEM

(71) Applicant: John Harp, Fort Smith, AR (US)

(72) Inventor: John Harp, Fort Smith, AR (US)

( * ) Notice: Subject to any disclaimer, the term of this patent is extended or adjusted under 35 U.S.C. 154(b) by 242 days.

(21) Appl. No.: 15/462,067

(22) Filed: Mar. 17, 2017

Related U.S. Application Data

(60) Provisional application No. 62/310,413, filed on Mar. 18, 2016.

(51) Int. Cl.
*C12Q 1/24* (2006.01)
*B01L 9/00* (2006.01)

(52) U.S. Cl.
CPC .................. *C12Q 1/24* (2013.01); *B01L 9/52* (2013.01); *B01L 2300/04* (2013.01); *B01L 2300/0803* (2013.01)

(58) Field of Classification Search
CPC ..... C12Q 1/24; B01L 9/52; B01L 2300/0803; B01L 2300/04
See application file for complete search history.

(56) References Cited

U.S. PATENT DOCUMENTS

| | | | | |
|---|---|---|---|---|
| 3,284,039 A | * | 11/1966 | Brunner | A47G 7/041 248/121 |
| 5,306,467 A | * | 4/1994 | Douglas-Hamilton | B01L 9/50 211/DIG. 1 |
| 6,251,624 B1 | | 6/2001 | Matsumura | |
| 7,296,379 B1 | * | 11/2007 | Peter | A01G 9/02 211/88.03 |
| 2006/0252299 A1 | * | 11/2006 | Daykin | C12M 23/10 439/409 |

OTHER PUBLICATIONS

Charnley, Low Friction Arthroplasty, 1979, p. 166.
Mollis, Total Hip Replacement without Deep Infection in a Standard Operating Room, The Journal of Bone and Joint Surgery, 1976, p. 446-450.
Ritter, Microbiological Studies in a Horizontal Wall-Less Laminar Air-Flow Operating Room During Actual Surgery, Clinical Orthopaedics and Related Research, 1973, p. 16-18.

* cited by examiner

*Primary Examiner* — Xin Y Zhong
(74) *Attorney, Agent, or Firm* — Wright Lindsey Jennings, LLP; Meredith Lowry; K. Brandon Middleton

(57) ABSTRACT

The present invention relates generally to a system for estimating the time related contamination of the sterile filed during surgical procedures. More specifically, the present invention employs the use of multiple settle plates on settle plate holders with a protective covers to hold the settle plate to prevent direct contact between the settle plate and surgical equipment.

7 Claims, 4 Drawing Sheets

QUANTITATIVE STERILE FIELD ANALYSIS SYSTEM

CROSS-REFERENCE TO RELATED APPLICATIONS

This application claims priority to and is a continuation-in-part of U.S. Provisional Patent Application Ser. No. 62/310,413 filed on Mar. 18, 2016, the disclosure of which is hereby incorporated by reference in its entirety.

STATEMENT REGARDING FEDERALLY SPONSORED RESEARCH OR DEVELOPMENT

Not Applicable.

REFERENCE TO A MICROFICHE APPENDIX

Not Applicable.

RESERVATION OF RIGHTS

A portion of the disclosure of this patent document contains material which is subject to intellectual property rights such as but not limited to copyright, trademark, and/or trade dress protection. The owner has no objection to the facsimile reproduction by anyone of the patent document or the patent disclosure as it appears in the Patent and Trademark Office patent files or records but otherwise reserves all rights whatsoever.

BACKGROUND

Under the Centers for Medicare & Medicaid Services (CMS) Bundled Payments for Care Improvement (BPCI) Initiative, which is becoming a required program in hospitals across the United States, healthcare providers are responsible for readmissions related to the index surgery for 30 days and eventually for 90 days. Although there may be a variety of reasons for patient readmission, surgical site infection is one of the leading causes for readmission. In addition, these surgical site infections can lead to further complications and must often be treated by antibiotics. Often times surgical site infections may even lead to the need of additional surgeries to correct the infection. In some applications, particularly those dealing with joint replacement, surgical site infections can lead to diminished functional outcome of the surgery and may even lead to permanent functional issues including limps, stiff joints, chronic infection, and even amputation.

Airborne contamination plays a primary role in the cause of surgical site infection. It was found in a study of 6000 patients that rigorous airborne and procedural contamination control could reduce the deep surgical site infection rate to 0.3-0.4%. This low rate of surgical site infection was achieved without the use of prophylactic antibiotics; whereas now it is estimated that surgical site infection rate after total join arthroplasty is nearly 1% (with a wide range of variation in the data) even with the use of prophylactic antibiotics. Although it is understood that several factors may play a role in the development of a surgical site infection, contamination control, particularly of airborne sources, still results in a dramatic increase in infection rate.

U.S. Pat. No. 6,251,624 issued to Matsumura et al. on Jun. 26, 2001 entitled Apparatus and method for detecting, quantifying and characterizing microorganisms, the disclosure of which is hereby incorporated by reference in its entirety, teaches a method for performing microbial antibiotic suspectibility testing. However, it fails to teach the testing within close proximity to specific areas of suspectibility for infection for the human body during surgery. It also does not teach a holder for containing the settle plates.

Although there have been techniques developed to control airborne contaminations in operating rooms, the success of these existing techniques can only be measured by observing the surgical site infection rates coming from these operating rooms. That is, the only way to currently determine whether airborne contamination occurred during a procedure is to wait until the patient develops a surgical site infection. This results in delayed feedback to the surgeon or hospital that there is a possible problem with the surgeon's techniques, supplies, or equipment. A system for providing feedback regarding the airborne contamination of an operating room closer to the actual time of surgery is desired.

BRIEF SUMMARY OF THE INVENTION

The present invention relates generally to a system for estimating the time related contamination of the sterile filed during surgical procedures. More specifically, the present invention outlines a process for measuring sterile field contamination in multiple zones of an operating room to reduce and eliminate surgical site infections caused by airborne contaminants. It is an object of the present invention to provide a near real-time measurement of the air contamination at the surgical site. It is a further object of the present invention to provide to hospitals a system for use in developing air quality standards to improve patient safety in operating settings. The details of the present invention will be described below.

BRIEF DESCRIPTION OF THE DRAWINGS

In the following drawings, which form a part of the specification and which are to be construed in conjunction therewith, and in which like reference numerals have been employed throughout wherever possible to indicate like parts in the various views.

DETAILED DESCRIPTION OF THE INVENTION

Figure 1:
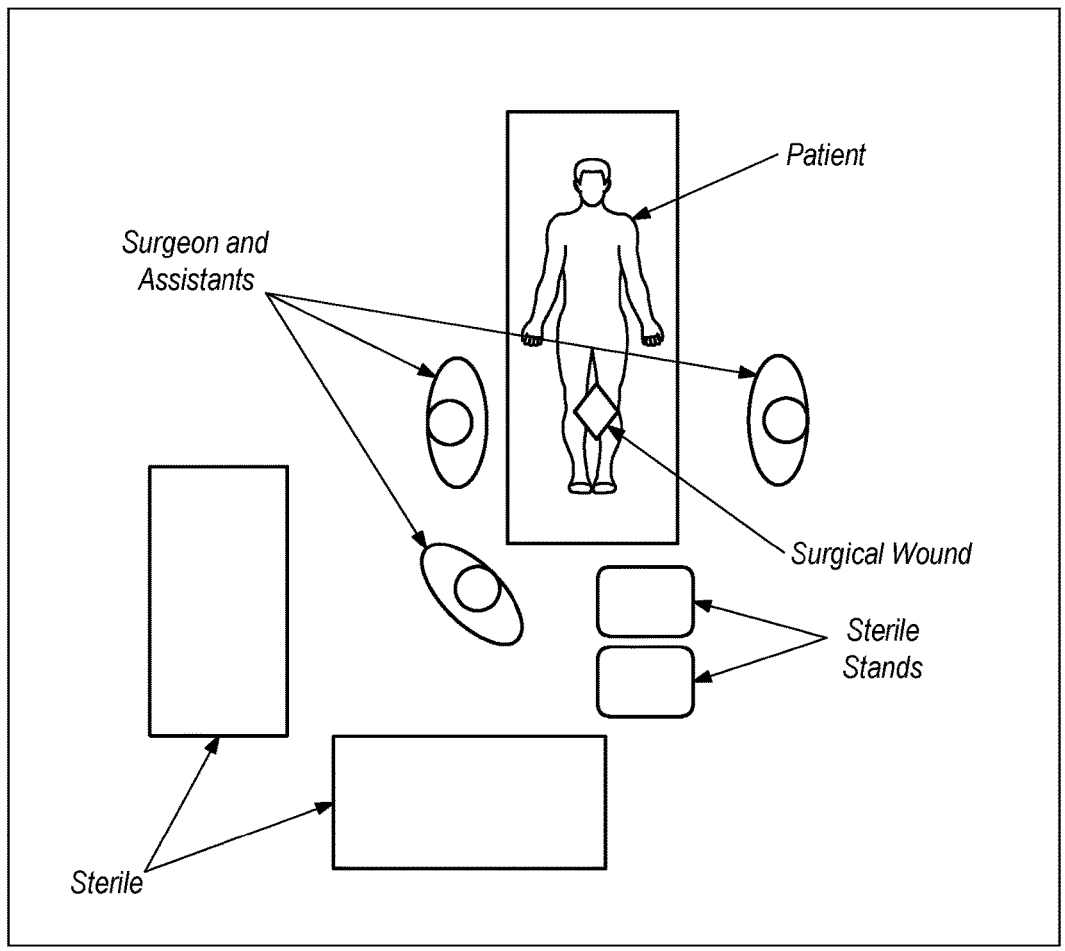
FIG. 1 is a schematic drawing of surgical procedure in an operating room.

Reference throughout this specification to "one embodiment", "an embodiment", "one example" or "an example" means that a particular feature, structure or characteristic described in connection with the embodiment or example is included in at least one embodiment of the present invention. Thus, appearances of the phrases "in one embodiment", "in an embodiment", "one example" or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

It will be understood that, although the terms first, second, etc. may be used herein to describe various elements, these elements should not be limited by these terms. These terms are only used to distinguish one element, from another element. For instance, a first element discussed below could be termed a second element without departing from the teachings of the present invention. Similarly, the second element could also be termed the first element.

The term "and/or" includes any and all combinations of one or more of the associated listed items. The terminology used herein is for the purpose of describing particular embodiments only and is not intended to be limiting. As used herein, the singular forms "a," "an" and "the" are intended to include the plural forms as well, unless the context clearly indicates otherwise.

It will be understood that when an element is referred to as being "coupled" or "connected" to another element, it can be directly coupled or connected to the other element or intervening elements may be present therebetween.

In contrast, it should be understood that when an element is referred to as being "directly coupled" or "directly connected" to another element, there are no intervening elements present.

It will be further understood that the terms "comprise", "include", "have", etc. when used in this specification, specify the presence of stated features, integers, steps, operations, elements, components, and/or combinations of them but do not preclude the presence or addition of one or more other features, integers, steps, operations, elements, components, and/or combinations thereof.

Unless otherwise defined, all terms including technical and scientific terms used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

The present invention relates generally to a system for estimating the time related contamination of the sterile filed during surgical procedures. More specifically, the present invention outlines a process for measuring sterile field contamination in multiple zones of an operating room to reduce and eliminate surgical site infections caused by airborne contaminants.

The present invention employs the use of multiple settle plates to measure airborne contaminants in an operating room. These settle plates, otherwise known as petri dishes, are sterile dishes of 90 mm in diameter or other sizes and are filled with a sterile nutrient substance, such as agar, that allows and promotes growth of bacteria landing on its surface. Airborne microbial contamination that has landed on the settle plate is incubated at the appropriate temperature for a specified amount of time will grow and become a visible mass, which for the description of the present invention will be termed a "colony forming unit (CFU)."

In order to achieve accurate measurements of airborne contaminants, the sampling system must first be set up and used to validate function of the operating room. This set-up procedure must be done when the operating room is "at rest," or when the ventilation and other equipment is present and functioning normally, but no personnel or patients are present. As part of the set-up procedure the air contamination at this "at rest" condition is measured. If the contamination for the "at rest" condition is zero, then the operating room is ready to be used for surgical case monitoring. If the air contamination is not zero for this "at rest" condition, the operating room conditions must be corrected to produce a zero contamination value for the "at rest" position. Once the conditions are corrected to produce a zero contamination value, the operating room is ready to be used for surgical case monitoring. A second part of the set-up procedure may be used to individualize sampling plans or protocols for that particular operating room and surgical procedure. These plans show the settle plate locations on sterile field and provide the appropriate timing for the opening and closing of the settle plates.

Figure 2:
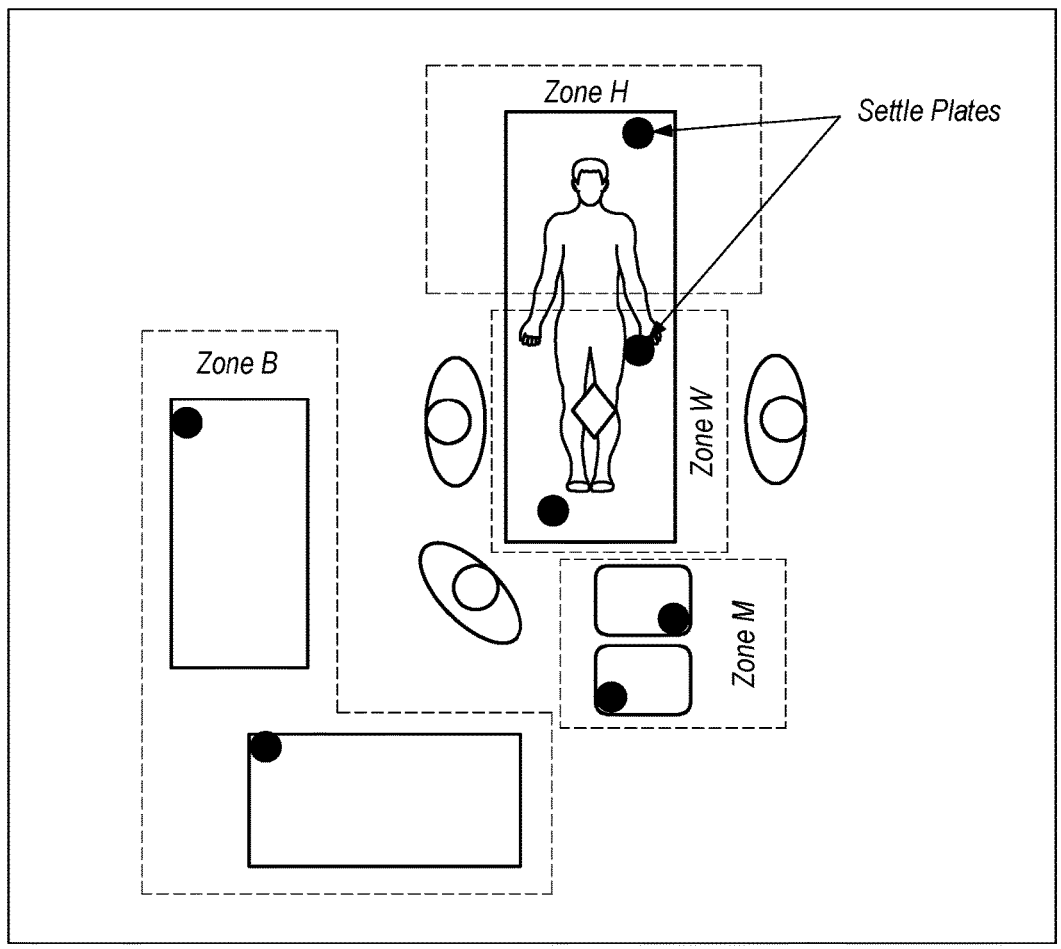
FIG. 2 is a schematic drawing of sampling zones of the present invention in a surgical operating room.

After the measuring of contamination values for the "at rest" condition reaches zero and the operating room is ready for surgery, the present invention is used for surgical case monitoring. This is a vital aspect of the present invention, as the measuring of the airborne contaminants during surgery will allow near real-time feedback to surgeons and hospitals on the operation of their surgical rooms. For surgical case monitoring, settle plates are placed on sterile field per preset sampling plans. These settle plates are preferably placed in a number of zones, as shown in FIG. 2. As shown in FIG. 2, settle plates are located in Zone H, near the head of the patient; Zone W in two locations, near the waist of the patient; Zone M in two locations, near the feet of the patient and near the medical tools; and Zone B in two locations. The placement of the settle plates will be based on the preset sampling plans, which will be different depending on the specific characteristics of the surgery and operating room. In order to maintain the sterility of the settle plates, the packaging containing a set of settle plates is opened by a scrubbed technician using a pair of bandage scissors or other aseptic technique. In another embodiment, the placement of the settle plates will be based upon preset sampling plans dependent upon pathogen characteristics of the surgery. The plates are opened, labeled with a sterile marking pen, and then placed in the appropriate sampling zone based on the preset sampling plan for that particular case. Other existing methods can be utilized such as bar codes to label plates and their positions.

The scrubbed technician or other human technician records case specific information for each plate. This information includes plate location, exposure time, case type, laterality, the surgeon's name, delay time if applicable, ancilliary equipment in use (such as patient warmers or suction units), operating information, and patient data, including age, sex, comorbidities, smoking statues, and body mass index. The collection of case specific information allows for the development of a more comprehensive analysis in conjunction with the colony morphology analyzed.

Figure 3:
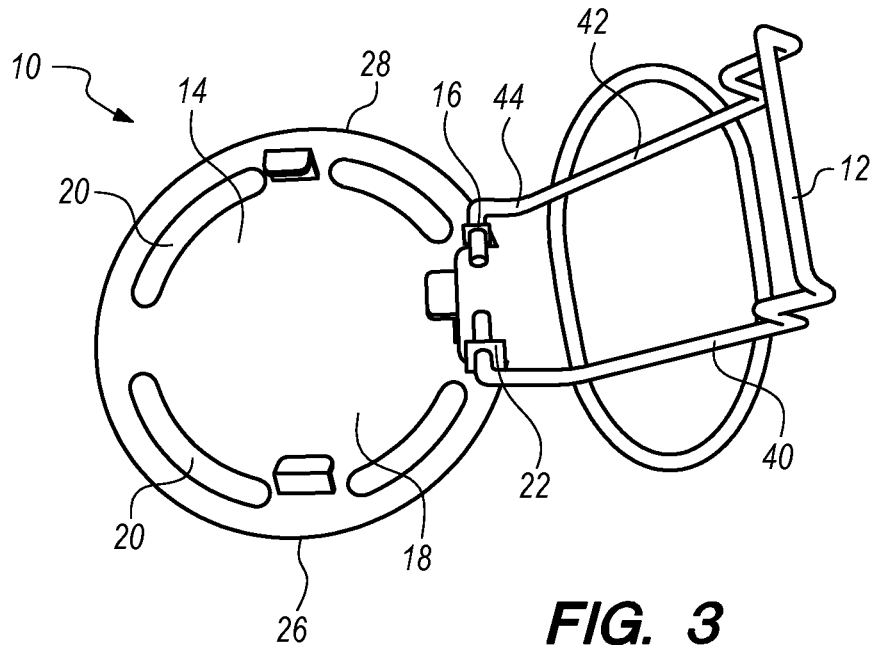
FIG. 3 is a photograph showing the settle plate holder of the present invention in the open position.
Figure 4:
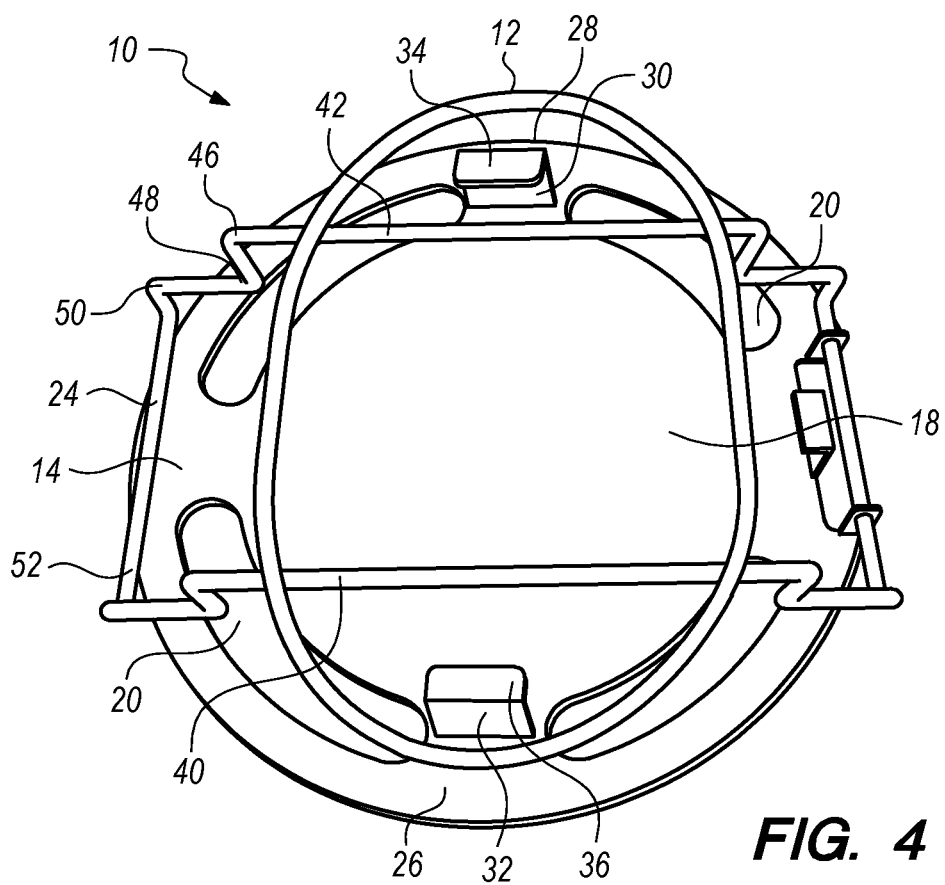
FIG. 4 is a photograph showing the settle plate holder of the present invention in the closed position.
Figure 5:
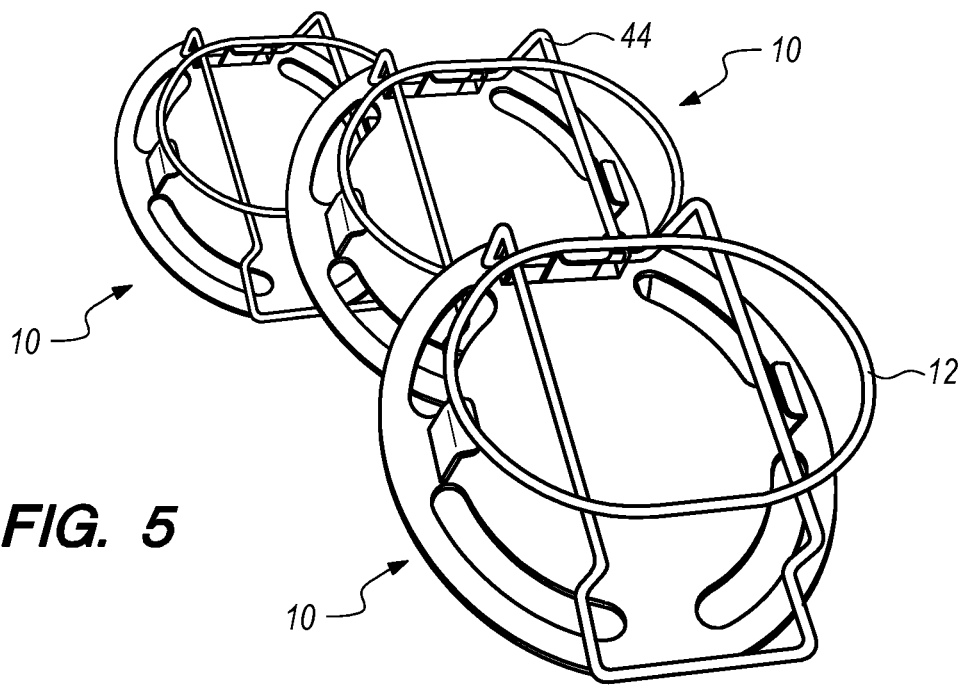
FIG. 5 is a photograph showing a set of three of the settle plate holders of the present invention.
Figure 6:
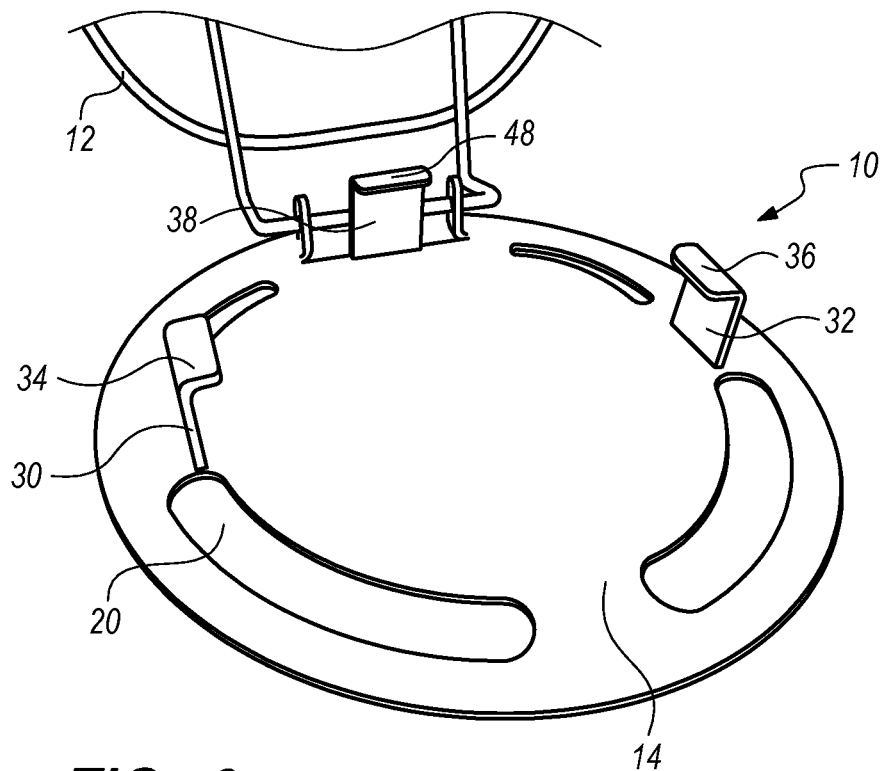
FIG. 6 is a photograph showing the settle plate holder of the present invention in the open position.

The plates are also opened and closed based on the preset sampling plan. As shown in FIG. 3-5, a settle plate holder 10 with a protective cover 12 is employed to hold the settle plate (not shown) to prevent direct contact between the settle plate and surgical equipment. The settle plate holder is stainless steel and built for repeat autoclave sterilization. The settle plate holder can be disassembled into two components for cleaning prior to sterilization if needed. A photograph of the settle plate holder 10 in its open position is shown in FIG. 3 and a set of three settle plate holders 10 is shown in FIG. 5. The settle plates are opened by removing the sterile glass or polycarbonate cover and storing it on the sterile field. The opened settle plate is then placed in the open settle plate holder 10 and the holder is configured in the closed position as shown in FIG. 4. The settle plates remain open in these holders for the duration of the surgical procedure. At the end of the procedure the holder in the closed position (FIG. 4) is reconfigured in the open position (FIG. 3) and the open settle plates are removed by the sterile technician the open settle plates are closed by applying the previously stored cover and the closed settle plates are collected and placed in an incubator for plate processing.

The settle plate holder 10 includes a planar base 14 having a circular or oblong base outline 18 with the protective cover 12 in hingeable arrangement with the base 14. A side of the base 14 includes the hinge 16 that connects the cover 12 to the base and allows the cover 12 to open to allow the placement of the settle plate proximate the center of the base outline 18 and then allows the cover 12 to pivot to close and bias the settle plate downward onto the base 14. In this arrangement, the settle plate is secured to the base 14.

The planar base 14 is a substantially solid sheet of stainless steel with four arcuate apertures 20 positioned proximate the exterior edge of the base 14 and spaced evenly along the circumference of the base 14. For orientation purposes, the hinge 16 is located along one side of the base, the back 22, and the opposing side of the base is the front 24. Proximate the edge of the left 28 and right 26 sides of the base 14 on each side are plate securing flanges 30, 32, 38 which extend perpendicular to the face of the planar base 14 to provide opposing flanges 30, 32, 38 to fit on either side of the settle plate. Each flange 30, 32, 38 has an upper abutting lip 34, 36, 48 that extends off the flange 30, 32 parallel to the base 14.

The cover 12 is an open construction to allow particulates access to the plates. The cover is composed of an arcuate wire centered upon two parallel arms 40, 42 which run from the hinge to the front of the base to secure to the front of the base when in a close position. The parallel arms extend upward perpendicularly from the base 14 at the hinge to a hinge joint 44 to then extend parallel across a substantial length of the base 14 from the hinge joint 44 to a front joint 46 proximate the front 24 of the base 14. A perpendicular arm 52 connects the parallel arms 40, 42 to form a closure that hooks over the edge of the base 14 when the cover is secured to the base 14.

The settle plates are incubated for a preset time at a preset temperature. The plates are interpreted by a human technician or through the use of an image processing system. The primary data recorded as a result of the interpretation is the number of colony forming units per settle plate (CFU/plate). Visual colony morphology data or other data derived from colony characteristics may prompt further lab tests to determine the actual species of the colony. Incubation time can be extended to identify different phenotype variations of bacteria such as "small colony variants". Plates are also examined for unusual clustering of colonies suggesting possible contamination from unusual sources. The data obtained from this plate processing may be used to determine the potential for surgical site infection caused by airborne contamination based on the time of exposure, the sampling zone, and the risk of wound contamination from sampling zone.

The data collected may be used to give direct feedback to the surgical team within 48 hours using current incubation techniques. The data produced potential for surgical site infection may be compared with the hospitals "acceptable values" or air contamination standards. In the event the data shows levels above acceptable values, the medical provider may seek patient specific interactions. For example, the doctor may provide the patient additional intravenous antibiotics or the patient may be asked to undergo irrigation and debridement surgical procedures.

The data collected may be tracked for short and long-term trends using statistical process control techniques. Observance of upward trends could indicate ventilation system problems in the operating room or sterile barrier issues requiring further investigation. The data collected at multiple hospitals for multiple cases may be combined to correlate with surgical infection patient outcomes. A statistical analysis on the data could result in determining allowable threshold levels for a given level of patient protection from surgical site infection. Statistical process control analysis techniques can then be applied to determine time related changes in contamination levels in the operating room and to both upper control limits and lower control limits for contamination levels.

What is claimed is:

1. A settle plate holder for a settle plate to collect airborne particulates in an operating room, said settle plate holder comprising:
   a planar circular base for securing a settle plate, said planar circular base having a top face and two opposing plate securing flanges extending perpendicularly from said top face and each having an upper abutting lip;
   said planar circular base devoid of a side wall; and
   a protective cover allowing airflow over a placed settle plate, said protective cover hingeably coupled to said planar circular base, said protective cover comprising two parallel arms extending across a substantial length of said planar circular base and an arcuate wire centered upon said two parallel arms.

2. The settle plate holder of claim 1, said planar circular base further having four arcuate apertures positioned proximate the exterior edge of said planar circular base in evenly-spaced distances along the circumference of said planar circular base.

3. A method for collecting airborne contaminents during surgery that involves the use of the device of claim 1, the method comprising the step of placement of at least one settle plate holder having a settle plate within a sterile field proximate a patient in a zone corresponding to an area of the body of the patient, said zone selected from group consisting of the patient head, the patient waist, the patient feet.

4. A settle plate holder for a settle plate to collect airborne particulates in an operating room, said settle plate holder comprising:
   a planar base for placement of a settle plate to collect airborne particulates, said planar base having an arcuate edge, a top face and three plate securing flanges extending perpendicularly from said top face, said three plate securing flanges each having an upper lip extending off of each flange and positioned proximate the exterior edge of said planar base;
   a protective cover allowing airflow over a placed settle plate, said protective cover hingeably coupled to said planar base and extending over said securing flanges when said protective cover is secured to said base, said protective cover comprising two parallel arms spaced apart from and extending across a substantial length of said planar base and an arcuate wire centered upon said two parallel arms; and
   a closure configured to secure said protective cover in a closed position over a settle plate.

5. The settle plate holder of claim 4, said planar circular base further having four arcuate apertures positioned proximate the exterior edge of said planar base in evenly-spaced distances along the circumference of said planar base.

6. A method for collecting airborne contaminents during surgery that involves the use of the device of claim 4, the method comprising the step of placement of at least one settle plate holder having a settle plate within a sterile field proximate a patient in a zone corresponding to an area of the body of the patient, said zone selected from group consisting of the patient head, the patient waist, the patient feet.

7. A settle plate holder for a settle plate to collect airborne particulates in an operating room, said settle plate holder comprising:
- a planar circular base having an arcuate edge, a top face and three securing flanges extending perpendicularly from said top face, said three securing flanges each having an upper lip extending off of each flange and positioned proximate the exterior edge of said planar circular base;
- a protective cover allowing airflow over a placed settle plate, said protective cover hingeably coupled to said planar circular base and extending over said securing flanges when said protective cover is secured to said base, said protective cover comprising two parallel arms spaced apart from and extending across a substantial length of said planar circular base and an arcuate wire centered upon said two parallel arms; and
- a closure configured to secure said protective cover in a closed position.

* * * * *